United States Patent [19]

Chervenelekov

[11] 4,406,624
[45] Sep. 27, 1983

[54] APPARATUS FOR PRODUCING TEMPORARY DENTAL CROWNS

[75] Inventor: Theo S. Chervenelekov, Sofia, Bulgaria

[73] Assignee: DSO "pharmachim", Sofia, Bulgaria

[21] Appl. No.: 297,579

[22] Filed: Aug. 31, 1981

[51] Int. Cl.³ .............................................. A61C 3/00
[52] U.S. Cl. ...................................... 433/156; 72/465
[58] Field of Search ................ 433/156, 34, 153, 154, 433/155, 162, 223; 72/57, 465, 347, 351, 352, 474; 29/160.6

[56] References Cited

U.S. PATENT DOCUMENTS

| | | | |
|---|---|---|---|
| 682,866 | 9/1901 | Asche | 72/351 |
| 906,911 | 12/1908 | McCullough | 72/57 |
| 1,012,401 | 12/1911 | McCullough | 72/57 |
| 1,507,476 | 9/1924 | Flanigan | 433/223 |
| 1,534,698 | 4/1925 | Gansert et al. | 72/57 |
| 3,705,512 | 12/1972 | Koschatzky | 72/57 |
| 3,916,525 | 11/1975 | Hirsch | 433/223 |
| 4,162,625 | 7/1979 | Simmons | 433/34 |

Primary Examiner—John J. Wilson

[57] ABSTRACT

Device for the production of temporary dental crowns having a die and a matrix. The die is an artificial tooth having a shape closely approximating that of the tooth being restored, a fixing and supporting shaft protruding from the middle of the artificial tooth. The matrix is cup-shaped with a recess into which an elastic ring is placed, the elastic ring pressing inwardly a plastic foil from which the temporary crown is formed about the die as it is thrust into the elastic ring. The relaxed internal diameter of the internal ring is smaller than the size of the lower part of the tooth being restored. Concentrically with the space in the open end of the matrix there is provided a socket with an outside flange within which the outer edge of the plastic foil is initially held. The device can produce temporary plastic dental crowns which closely approximate the shape of the tooth being restored, and it is easy to take the crown off the matrix and the die without any damage thereto.

2 Claims, 1 Drawing Figure

U.S. Patent  Sep. 27, 1983  4,406,624
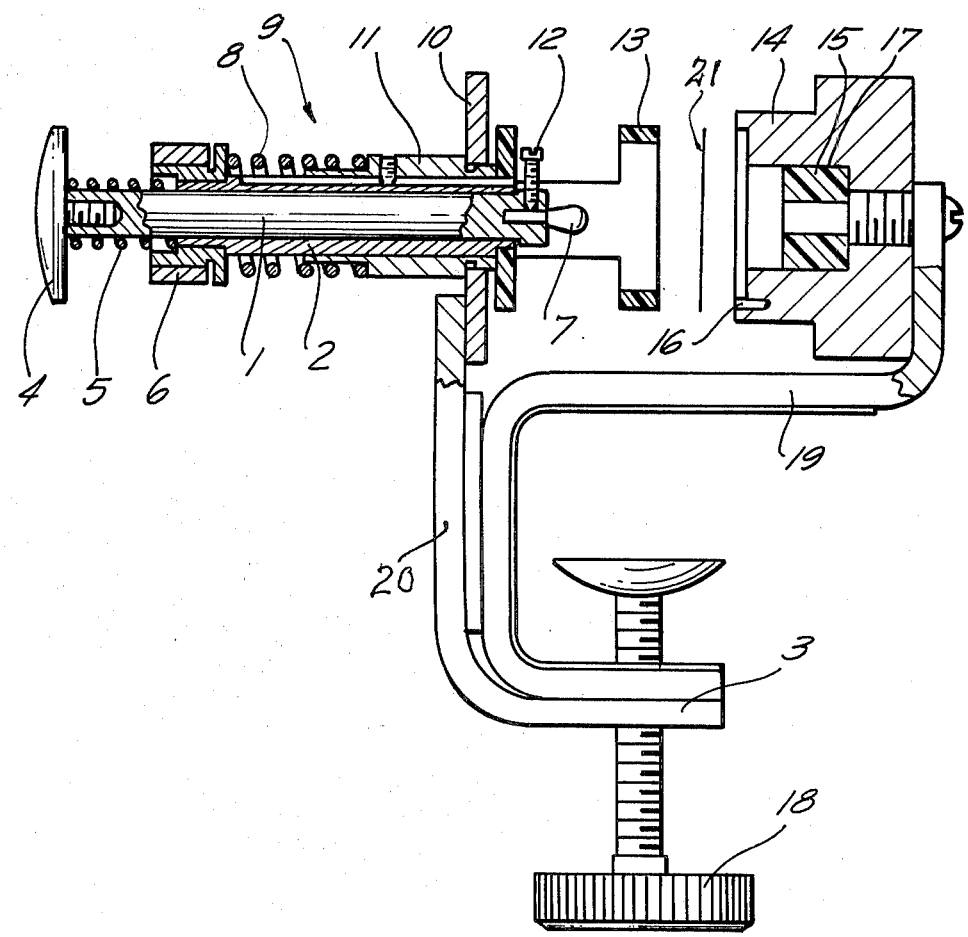

APPARATUS FOR PRODUCING TEMPORARY DENTAL CROWNS

This invention relates to apparatus for the production of temporary dental crowns, which are used in everyday dental practice, as for the one-visit restoration of broken teeth, and for the protection of filed teeth during dental restorations.

A device is known for the production of temporary dental crowns, such device being a vacuum press with an opening matrix. Such device produces temporary dental crowns by vacuum from plastic foil which has been softened in advance.

A disadvantage of such known device is that it produces a series of standard crowns which are rather difficult to fit to a broken tooth, due to the fact that during the production of the temporary crown the individual characteristics of the tooth involved have not been taken into account. As a result, around the tooth being restored there may accumulate a large quantity of material, or the space around the tooth may not be sufficiently filled, either of which conditions leads to trauma and inflammation of the gum.

A method for the production of cast metal crowns is known; in such method a crown is made from plastic foil in an intermediate stage, the crown resulting from such intermediate stage being filled with gypsum whereby to form a die which is used for the casting of the metal crown. The device for the production of the plastic crowns includes a gypsum die with the shape of a tooth, and a matrix which is cup-shaped and filled with plastic material.

A disadvantage of the device described immediately above is that the plastic crown cannot be taken off the gypsum die without damage, since the upper part of the plastic crown is wider than the lower part of the tooth.

The invention has among its objects the provision of a device without the above-named disadvantages of known devices, which will insure the production of temporary dental crowns which have a shape that closely approximates the shape of the tooth being restored, and which produces a temporary dental crown which can easily be taken off the die without causing any damage thereto.

The above objects are achieved by the device according to the invention, such device having a die and a matrix. The die is an artificial tooth having a shape closely approximating that of the tooth being restored, a fixing shaft protruding from the middle of the artificial tooth. The matrix is cup-shaped with a recess into which an elastic ring is placed, the elastic ring pressing inwardly the plastic foil from which the temporary crown is to be formed. The relaxed internal diameter of the internal ring is smaller than the size of the lower part of the tooth being restored. Concentrically with the space in the open end of the matrix there is provided a socket with an outside flange.

With the aid of a stand, the matrix is affixed to an aligned holder which contains a plunger, a cylinder, and a sleeve, all of which are disposed concentrically to each other. A die is affixed to one of the ends of the plunger, the opposite end of the plunger being shaped as a push button. At one end of the cylinder there is disposed a diaphragm, while at the other end of the cylinder there is disposed a nut. To the sleeve there is affixed a flange through which the holder is affixed to the stand. Springs are disposed between the push button and the nut, on the one hand, and between the nut and the face of the sleeve.

The above-described device has the following advantages: It can produce temporary plastic dental crowns which closely approximate the shape of the tooth being restored, and it is easy to take the crown off the matrix and the die without any damage thereto.

A preferred embodiment of the device of the invention is shown in the single FIGURE of the drawing, which is a view partially in side elevation and partially in longitudinally axial section.

The device of the invention has a stand 3 which is adapted to be mounted on the edge of a support such as a table. The support 3 has an upper horizontal portion 19 and opposing clamping foot mounted upon a vertical screw having a thumb wheel 18 affixed to the lower end thereof. Beyond the horizontal part 19 of the stand 3, the stand is bent into a vertical portion to which there is affixed a matrix 14. The stand 3 has another vertical portion 20, a holder 9 being affixed to the upper end of part 20 through a vertical flange 10. The matrix 14 and the holder 9 are disposed coaxial of each other.

The matrix 14 is cup-shaped, within the space 17 within the matrix there being disposed an elastic ring 15, the axis of the central opening in the ring being coaxial with that of the matrix 14 and the holder 9. The internal diameter of the ring 15 is somewhat smaller than that of the lower part of the tooth being restored. The inner surface of the opening in the ring 15 provides a radially inwardly directed pressure on the foil from which the temporary dental crown is being made. Concentrically with the circular cylindrical space 17 of the matrix 14 there is provided a socket 16 having a circular rim or flange directed toward the holder 9.

The holder 9 has a plunger 1, a cylinder 2, and a sleeve 11, all of such parts being concentric with each other and with the axis upon which the matrix 14 and the holder 9 are located. The end of the plunger 1 confronting the matrix 14 has a central blind bore therein which receives the shaft of a die 7, the shaft being retained in such bore by a set screw 12. The other, outer end of the plunger 1 has a push button 4 affixed thereto. The cylinder or sleeve 2, within which the plunger 1 reciprocates, has a nut 6 screwed thereonto at its outer end, and a diaphragm-engaging clamping means 13 secured thereto at its other end. The cylinder or sleeve 2 is slidably mounted within an annular member 11 to which the member 10 is secured. A first coil compression spring 5 is disposed between the push button 4 and the outer end of the sleeve 2, and a second coil compression spring 8 is disposed between the nut 6 and the annular member 11. It is to be noted that the compressive strength of the spring 8 markedly exceeds that of the spring 5.

The above described device operates as follows:

The stand 3 is mounted upon a table and is clamped thereto by the means 18. An artificial tooth is selected which will serve as a die 7, such artificial tooth having a shape that closely approximates the shape of the tooth being restored. The artificial tooth is additionally machined in order to give it the individual characteristics of the tooth being restored. The die 7 is affixed to the plunger 1 by the set screw 12. A sheet 21 of plastic foil, which has been pre-heated, is disposed within the socket 16 of the matrix 14 and is retained therein by pushing the push button 4 to the left, thereby advancing the sleeve 2 and the annular presser member 13 affixed thereto to the right. The presser member 13 enters the socket 16 and clamps the peripheral edge of sheet 21 between it and the annular transverse surface of socket 16.

Further pressing of the push button 4 to the right, after the push button has engaged the left-hand end of the nut 6, results in the thrusting of the plunger 1 to the right and the compressing of the spring 8. The die 7 now sinks, together with the plastic foil, into the central opening in the elastic ring 15. As a result of the pressing force produced by the elastic ring 15 upon the plastic foil and the die 7, the foil takes the shape of the die 7. The push button 4 is now released, and the springs 5 and 8 return the die 7 and the diaphragm-clamping member 13 to their initial positions. The plastic temporary crown remains in the opening in the elastic ring 15, from which it can readily be extracted.

Although the invention is illustrated and described with reference to one preferred embodiment thereof, it is to be expressly understood that it is in no way limited to the disclosure of such preferred embodiment but is capable of numerous modifications within the scope of the appended claims.

I claim:

1. A device for the production of temporary dental crowns, comprising a male die having the substantial shape of the tooth to be restored, means for mounting the male die, a female die aligned with the male die and comprising an elastic ring, a holder for the elastic ring, means for holding a piece of plastic foil from which the temporary crown is to be formed between the male and female die, comprising an annular seat on the holder surrounding the path of relative movement of the male and female dies, said seat receiving the outer edge of the piece of plastic foil, and means for advancing the male and female dies relatively toward each other along a path whereby the plastic foil is thrust into the elastic ring and about the male die to form the temporary crown, an annular means on the means for mounting the male die, said annular means being coaxial of the path of relative travel of the male and female dies and fitting into the annular seat on the holder for the elastic ring whereby to grip the edge of the plastic foil between it and the said seat, the female die being fixedly mounted and the male die and the annular means receivable in the seat on the holder for the female die being mounted on plungers which reciprocate toward and away from the female die, and means for first moving the plunger which mounts the annular member toward the female die and for thereafter moving the male die toward the female die.

2. A device according to claim 1, wherein the inner diameter of the relaxed elastic ring is smaller than the diameter of the smallest part of the male die.

* * * * *